(12) United States Patent
Wiesinger

(10) Patent No.: US 11,103,658 B2
(45) Date of Patent: Aug. 31, 2021

(54) SYSTEM AND METHOD FOR SALT HOLDING INTEGRATABLE PILLOW

(71) Applicant: Paulette K. Wiesinger, Edgewood, WA (US)

(72) Inventor: Paulette K. Wiesinger, Edgewood, WA (US)

( * ) Notice: Subject to any disclaimer, the term of this patent is extended or adjusted under 35 U.S.C. 154(b) by 0 days.

(21) Appl. No.: 17/131,054

(22) Filed: Dec. 22, 2020

(65) Prior Publication Data

US 2021/0196907 A1 Jul. 1, 2021

Related U.S. Application Data

(60) Provisional application No. 62/955,386, filed on Dec. 30, 2019.

(51) Int. Cl.
| | | |
|---|---|---|
| A61K 9/00 | (2006.01) | |
| A01K 5/00 | (2006.01) | |
| A61M 15/08 | (2006.01) | |
| A61M 21/02 | (2006.01) | |
| A61M 15/00 | (2006.01) | |
| A61D 7/04 | (2006.01) | |
| A61B 17/32 | (2006.01) | |
| A61K 33/14 | (2006.01) |

(Continued)

(52) U.S. Cl.
CPC ......... *A61M 15/0001* (2014.02); *A01K 5/008* (2013.01); *A01K 5/015* (2013.01); *A61B 17/32* (2013.01); *A61D 7/04* (2013.01); *A61K 9/0075* (2013.01); *A61K 33/14* (2013.01); *A61K 47/02* (2013.01); *A61K 47/46* (2013.01); *A61M 21/02* (2013.01); *A61B 2017/320004* (2013.01); *A61M 2021/0016* (2013.01); *A61M 2021/0077* (2013.01); *A61M 2209/088* (2013.01); *A61M 2210/0606* (2013.01); *A61M 2250/00* (2013.01)

(58) Field of Classification Search
CPC ... A47C 21/026; A23K 10/40; A47L 2501/07; A61H 33/04
See application file for complete search history.

(56) References Cited

U.S. PATENT DOCUMENTS

| | | |
|---|---|---|
| 2018/0104518 A1 | 4/2018 | Lee |
| 2019/0083395 A1* | 3/2019 | Doshi ............... A61M 15/0003 |

FOREIGN PATENT DOCUMENTS

| | | | |
|---|---|---|---|
| CN | 105288859 A | * | 2/2016 |
| CN | 206836301 | | 1/2018 |

(Continued)

OTHER PUBLICATIONS

"Halotherapy Mask," https://www.instructables.com/id/Halotherapy-Mask/. date accessed: Aug. 28, 2019.

*Primary Examiner* — Christine H Matthews
*Assistant Examiner* — Joshua Daryl D Lannu
(74) *Attorney, Agent, or Firm* — Christopher Mayle; Bold IP, PLLC

(57) ABSTRACT

A system and method for a salt holding integratable pillow having wool infused with different types of salts, particularly Pharmaceutical grade salt ground into a powder and essential oils that may be integrated into masks, scrubbing sleeves used by athletes and other people for performance, baby toys, cat toys for asthmatic felines, small pillows, pillow cases acting as a salt holding device, feed bag styles having salt holding devices for horses and other animals.

11 Claims, 8 Drawing Sheets

(51) Int. Cl.
*A61K 47/46* (2006.01)
*A61K 47/02* (2006.01)
*A01K 5/015* (2006.01)
*A61M 21/00* (2006.01)

(56) References Cited

FOREIGN PATENT DOCUMENTS

| | | | |
|---|---|---|---|
| JP | 2002300953 A | * | 10/2002 |
| JP | 2013220248 | | 10/2013 |
| KR | 101564656 | | 10/2015 |

* cited by examiner

SYSTEM AND METHOD FOR SALT HOLDING INTEGRATABLE PILLOW

CROSS REFERENCE TO RELATED APPLICATIONS

This application is a non-provisional application which claims priority to U.S. Provisional Application No. 62/955,386 filed on Dec. 30, 2019, which is incorporated by reference in its entirety.

FIELD OF DISCLOSURE

This invention relates to Halotherapy, and more specifically, to a salt holding integratable pillow which may be employed by apparatuses such as masks, feed bags, toys, and any other item. The salt holding pillow is created with layers of wool fibers infused with salts, and for Aromatherapy, essential oils, to provide the wearer, human or animal, with the therapeutic benefits of Halotherapy or salt therapy and in the case of using Aromatherapy, and essential oils.

BACKGROUND

According to World Health Organization, in 2017 approximately 235 million people are suffering from asthma worldwide. Among the people, most suffering are children and people living in poverty. Additionally, more than 65 million people around the world have moderate or severe chronic obstructive pulmonary disease (COPD). Experts predict that this number will continue to rise worldwide over the next 50 years.

Halotherapy has been commonly used to help with allergies or pulmonary diseases. The term "Halotherapy" comes from "halo", the Greek word for salt. For centuries, people in Poland used naturally-occurring salt caverns to treat respiratory ailments and salt miners rarely had any respiratory illness. Halotherapy with the use of, in particular, Pharmaceutical Grade Salt have had favorable effects when treating respiratory ailments, skin irritations, and mental lethargy. Athletes use Halotherapy for better performance. Halotherapy has also been shown to relieve allergies, help with stuffiness, and is used for antibacterial purposes, and promote adequate airflow and sleep. Halotherapy is common with race horses as they need more salt, there are mobile treatment stations and salt blowing machines. The common problems with halo therapy are that these types or resources are only provided at spa sites, remote locations or limited mobile units. There are some that are portable but may be problematic for any electrical devices or appliances in the room regarding corrosion from the salt. Those portable machines may also be cumbersome.

SUMMARY

The disclosure presented herein relates to a salt holding apparatus, the salt holding apparatus having one or more wool layers of fiber, the layers infused with salt and essential oils, the one or more wool layers made of wool fibers that have been pulled apart and formed to create a rectangular or any other shape, wherein the salt is pharmaceutical grade salt, pink Himalayan salt, or sea salt, wherein the salt is blasted or poured or sprayed or mixed in, in any fashion the one or more wool layers, wherein the salt is ground into a powdered form, the one or more wool layers having multiple receiving slots for receiving the salt and the essential oils, the receiving slots positioned at specific elevations, wherein the salt is positioned between a first layer of the one or more wool layers and a second layer of the one or more wool layers is of smaller size than the salt positioned between the second layer of the one or more wool fibers and a third layer of the one or more wool layers, wherein the one or more wool layers are rolled into one or more rolls, wherein the salt holding pillow is removably inserted into a pocket of a facial mask, the pocket positioned inside of a nose cover of the facial mask, wherein the salt holding pillow is positioned into an interior of a stuffed toy, wherein the salt holding pillow is integrated into an interior of a feeding mask, the feeding mask connected to a head strap, the head strap configured to be positioned around a head of a horse, the salt holding apparatus, further comprising a self-fastening wrap, wherein the salt holding pillow is configured to be positioned between the wrap and a users' body, wherein the salt holding pillow is integrated into one or more intermediate layers of a sleeping-bag type roll, the sleeping-bag type roll having an exterior and interior layer, the one or more intermediate layers positioned between the exterior and interior layer form a structure defining an elongated, rectangular configuration.

The disclosure presented is also directed to a salt holding pillow, the pillow having a first section having a first wool layer and a second wool layer positioned above the first wool layer as a table formation, salt then placed on the second wool layer, the first section further comprising a third wool layer positioned above the salt, the second section identical to the first section positioned above the first section, the wool layer made of wool fibers that have been pulled apart and formed to create a rectangular shape, wherein the salt is pharmaceutical grade salt, pink Himalayan salt, or sea salt, wherein the salt is ground into a powder.

BRIEF DESCRIPTION OF DRAWINGS

The present invention will be described by way of exemplary embodiments, but not limitations, illustrated in the accompanying drawings in which like references denote similar elements, and in which.

DETAILED DESCRIPTION

Figure 1:
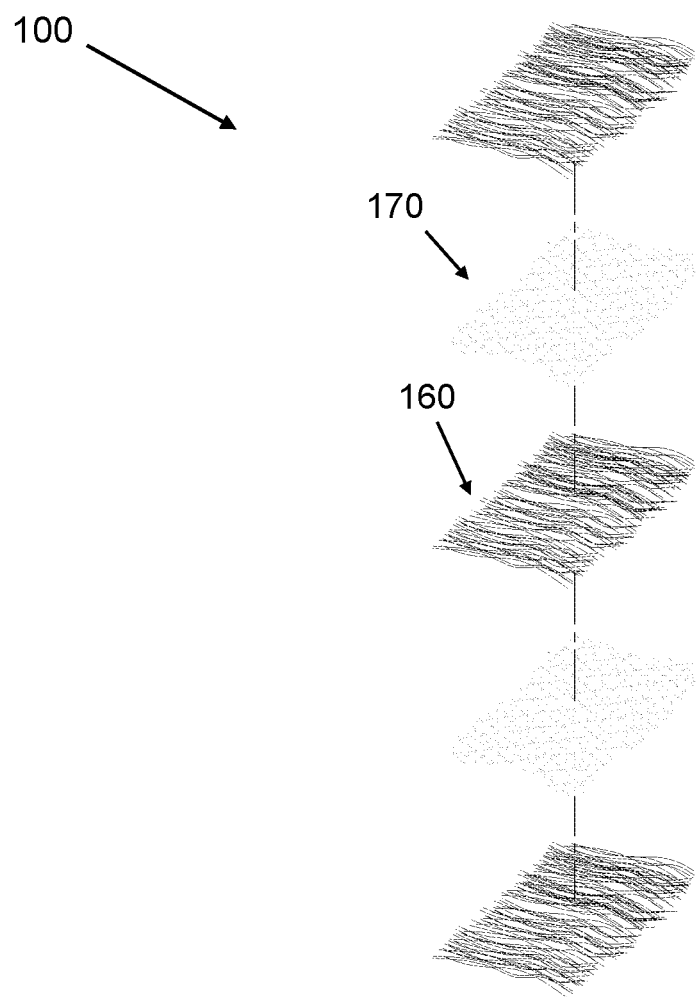
FIG. 1 is an illustration showing the various embodiments of the salt holding pillow and the combinations of salt mixed in and held by a wool layer.

In the Summary above and in this Detailed Description, and the claims below, and in the accompanying drawings, reference is made to particular features of the invention. It is to be understood that the disclosure of the invention in this specification includes possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item, so a "set of items" may indicate the presence of only one item, or may indicate more items. Thus, the term "set" may be equivalent to "one or more" as used herein.

The present disclosure recognizes the unsolved need for a personal salt holding integratable device by having wool infused with different types of salts and essential oils. These may take the form but are not limited to attachable/insertable pillows for face masks, for portable treatments and may be used by athletes and other people for performance, baby toys, cat toys for asthmatic felines, small pillows, pillow cases acting as a salt holding device, feed bag style having salt holding devices for horses and other animals. Wool is designed to hold the salt in place. When the salt holding pillow is encased in a mask, stuffed toy (not for teething), cat toy, or horse feed bag and is orientated over the user's mouth the user may breathe in and out moving the salt into the respiratory system thus promoting cleansing relief scrubbing for different lung ailments and other conditions of the user.

FIG. 1 is a perspective view of an embodiment of salt holding pillow system 100 of the present invention that may be insertable into various apparatuses such as masks, stuffed animals, feed bags, handbags and other items.

Referring to FIG. 1, salt holding pillow system 100 may have one or more layers built into or positioned inside salt holding pillow system 100. Salt holding pillow system 100 may have an exterior surrounding housing made of wool, or other fibers, to hold the various layers such as wool fibers 160. However, this is non-limiting and other fibrous material such as cotton, bamboo, flax, kenaf, hemp, or straw may be used. The wool fibers may be infused with salts such as salts 170. Salt 170 may be pharmaceutical grade salt, pink Himalayan salt, sea salt, or any other form of therapeutic, or smoked or enhanced with essential oils, salt. Salt 170 may be manufactured into any shape or size, as necessary. Salt 170 may be of substantially the same density and consistency in bulk such as grounded into a powdered form. Salt 170 may be impregnated into the wool fibers, by a natural binding process provided by the wool itself by having scales. Salt 170 may be of relatively small size particles such that the general texture and feel of the layer and wool fiber layers are not altered. In some embodiments salt 170 may be instead blasted or sprayed into the and wool fibers.

In some non-limiting embodiments pristine wool is layered or formed into balls or inserted into a cover whereby powdered Pharmaceutical grade salt is added to the wool.

In some embodiments the wool may also hold salt 170 as the wool has scales which catches salt. Wool springs back, this spring-back ability keeps good airflow by keeping pillow system 100 from padding up. An amount of salt 170 may then be placed on wool. This process may be repeated multiple times. The wool is then rolled up and placed into pocket 140 or used in another salt holding apparatus.

Wool fibers or layers may also be infused with essential oils in a similar manner to salt 170. The effect the essential oils may have on the user depends upon the specific types of the oils. For instance, rosemary may be used for increased memory absorption or lavender may be sued for a resting, calming effect. In some embodiments rice or silica may be added and used as a desiccant.

In other embodiments wool rectangular layers 160 may be comprised of multiple receiving slots extending from the front surface to back surface for receiving salt 170 and essential oils. The receiving slots may be configured to receive salt 170 and essential oils and are tubular in shape. The receiving slots are not limited to this shape and may also be a square, rectangle, hexagon, or octagon. The receiving slots may extend up to the width of the wool rectangular layers 160. The receiving slots may be cylindrical but may be customizable for various types of salt and essential oils as well as the application needed. The slots may be positioned at specific elevations to uniformly circulate salt 170 when breathing.

Figure 2:
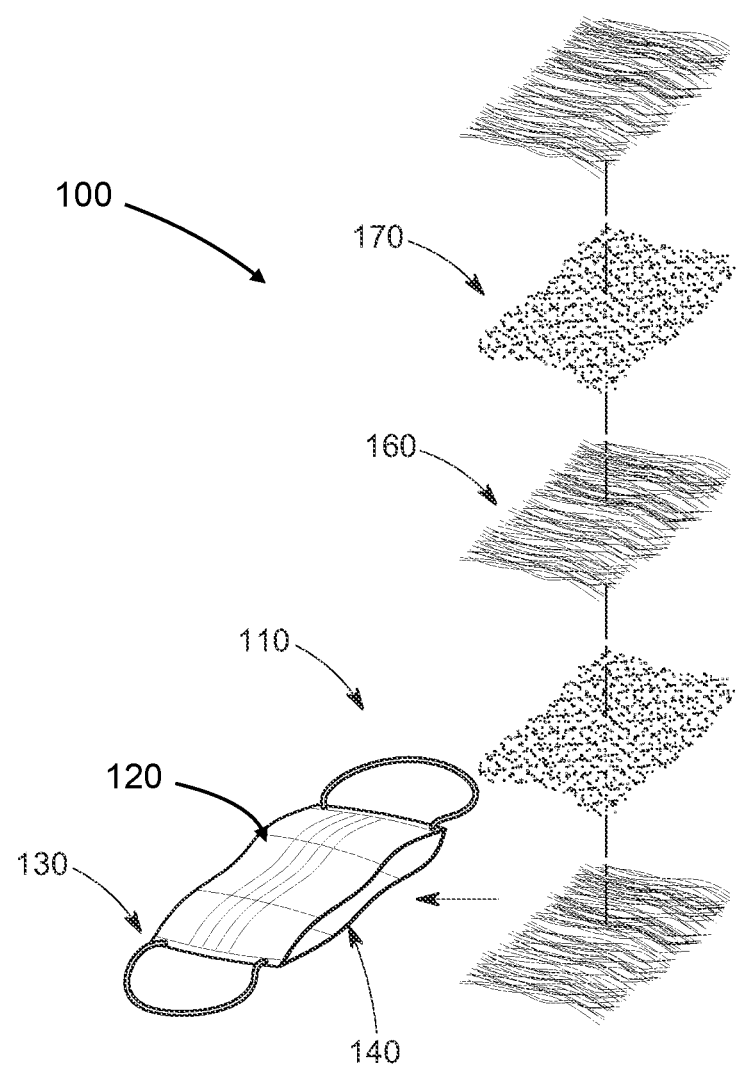
FIG. 2 is an illustration showing the salt holding pillow integrated into a facial mask.

In some non-limiting embodiments salt holding pillow system 100 may be inserted into a state-of-the-art face mask such as face mask 110 as illustrated in FIG. 2. Face mask 110 may have a nose and mouth cover 120 or protector with two ear loops 130 coupled at opposite ends of nose and mouth cover 120. Nose and mouth cover 120 may be rectangular shape. However, this is non-limiting and nose and mouth cover 120 may be square, circular, oval, hexagonal, octagonal or any other shape suitable for the purpose of the present invention. The user may be a human, animal, or other entity. In other embodiments face mask 110 may be any type of mask secured to user by Velcro®, tied rope, buttons, or any other method known by those of ordinary skill in the art.

Ear loops 130 act as a securing mechanism to position and attach the mask to a user's face. In some non-limiting embodiments ear loops 130 may include one or more bands of resilient material having a greater modulus of elasticity than that of nose and mouth cover 120, whereby the bands at both ends may be secured proximally against the outer perimeter of nose and mouth cover 120 such as at the upper and lower corners. The resilient material for the bands may be selected according to their modulus of elasticity to tightly engage each of the lines of dependency such that face mask 110 may remain firmly engaged against the back of user's ears when wrapped around the users user's ears and then released.

In some embodiments nose and mouth cover 120 may include an opening on the top surface with no openings on the left, right, and bottom surfaces, producing a pocket 140. In some embodiments pocket 140 may be attached to the back of the nose and mouth cover 120. Pocket 140 may be adapted to hold salt holding pillow system 100. Pocket 140 may be designed so that when salt holding pillow system 100 is positioned within pocket 140, the elastic material of pocket 140 may gently compress the layers of fibers 170 to secure them without damaging or altering the layers. Once salt and essential oils have been introduced into the and wool fibers the opening may be sealed shut with a sewing device. However, this is non-limiting and salt holding pillow system 100 may be attached to face mask 110 by any form of fasteners known by those of ordinary skill in the art such as but not limited to zippers, adhesive, latches, Velcro®, or hinges as well as positioned between the mask and the user's nose and mouth when in use.

Figure 3:
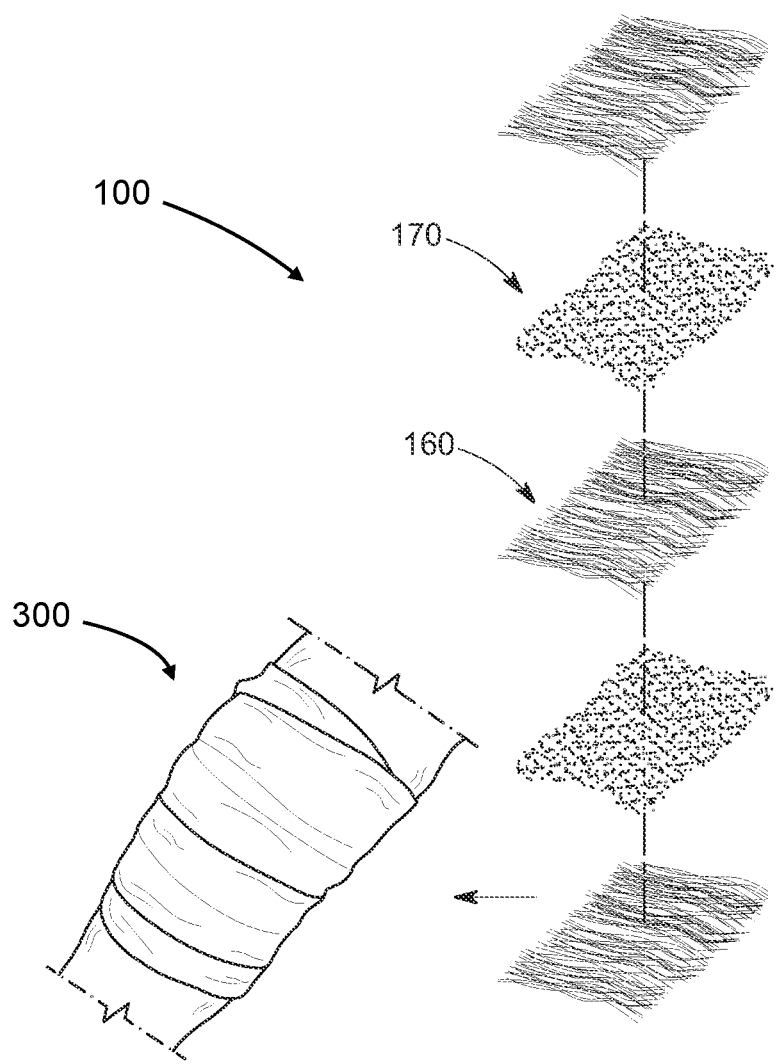
FIG. 3 is an illustration showing the salt holding pillow integrated into a scrubbing sleeve.

In one or more non-limiting embodiments, salt holding pillow system 100 may be incorporated into a self-fastening wrap, as illustrated in FIG. 3, to also provide additional scrubbing for the painful and inflamed areas of a user's body such as their arm, leg, or foot as well as atopic dermatitis, allergic dermatitis, eczema, or psoriasis. This may be accomplished by the user holding the loose end of the wrap and begin wrapping the wrap at a spot on the user's body, keeping it lightly taut with a slight pull. When approaching the affected area the user wraps the wrap around salt holding pillow system 100 so it stays in place between the wrap and the affected area. User may then continue to wrap the wrap to cover the entire area and then attach the other loose end to the remainder of the wrap to secure the wrap on the user's body.

In one or more non-limiting embodiments, salt holding pillow system 100 may be incorporated into a scrubbing sleeve using additive manufacturing processes such as scrubbing sleeve 300, to provide additional scrubbing for the painful and inflamed areas of a user's body such as their arm, leg, or foot as well as atopic, dermatitis, allergic dermatitis, eczema, or psoriasis. Scrubbing sleeve 300 is tailored and constructed so that it provides additional scrubbing to the body part. Scrubbing sleeve 300 may be seamless and use the density of knit stitches combined with yarns that have the properties of stretch, rigidity, compression, microbial, anti-bacterial, heating, cooling, anti-inflammatory, and moisture wicking to provide compression, scrubbing, stability, and comfort to the user. Scrubbing sleeve 300 may have additional rigidity for firm scrubbing to protect the user's body.

In one or more non-limiting embodiments, salt holding pillow system 100 may be removable, held in a scrubbing sleeve 300, as illustrated in FIG. 3, where salt holding pillow system 100 may be found one layer down from the top layer of the outside fibers of scrubbing sleeve 300 but above inner layers having moisture-wicking anti-bacterial fibers. In one or more embodiments, salt holding pillow system 100 may be knitted or sewn into the scrubbing sleeve as a non-removable integral part. In one or more embodiments, salt holding pillow system 100 may be secured in the scrubbing sleeve with a fastener, such as a button, strap, zipper, Velcro® or any other fastening means. While knitted or secured into scrubbing sleeve 300, salt holding pillow system 100 may be orientated to provide relief to the user.

Figure 4:
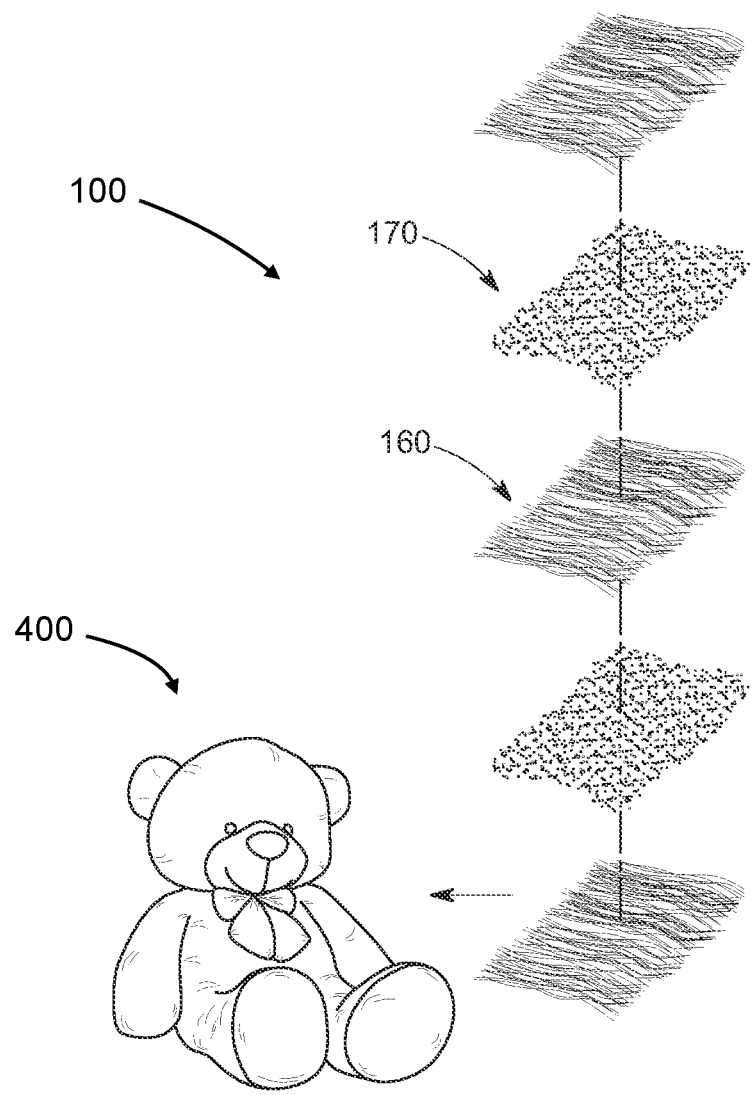
FIG. 4 is an illustration showing the salt holding pillow integrated into a stuffed animal.
Figure 5:
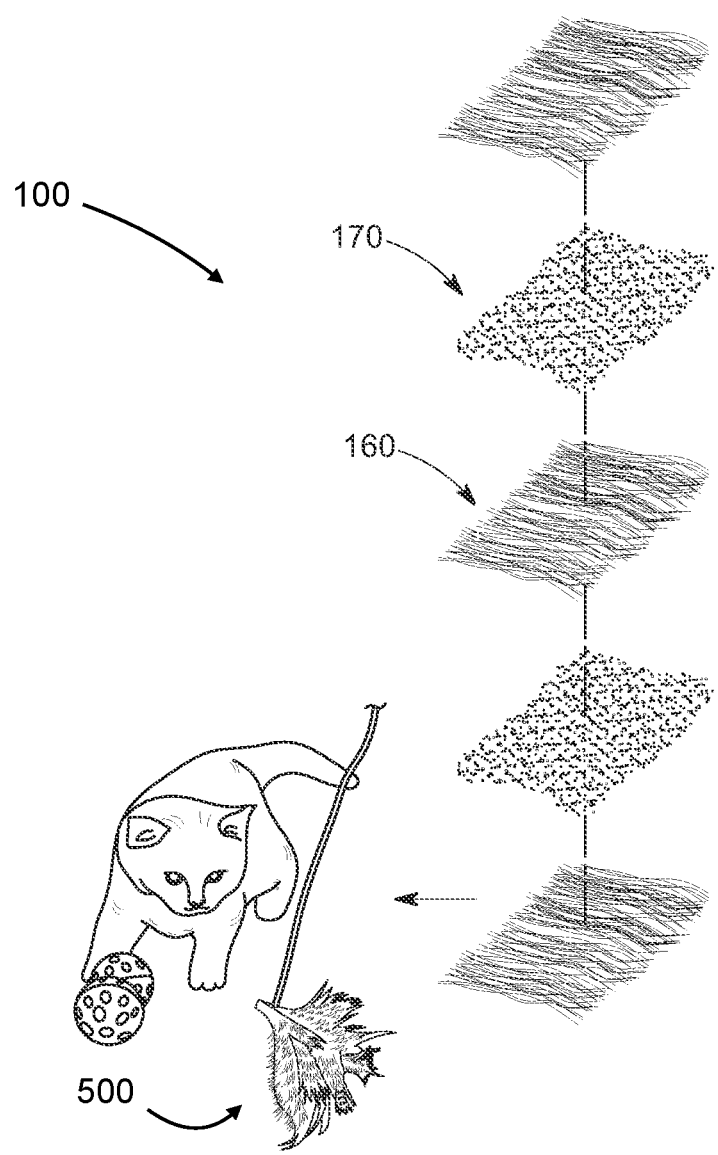
FIG. 5 is an illustration showing the salt holding pillow integrated into a cat toy.
Figure 8:
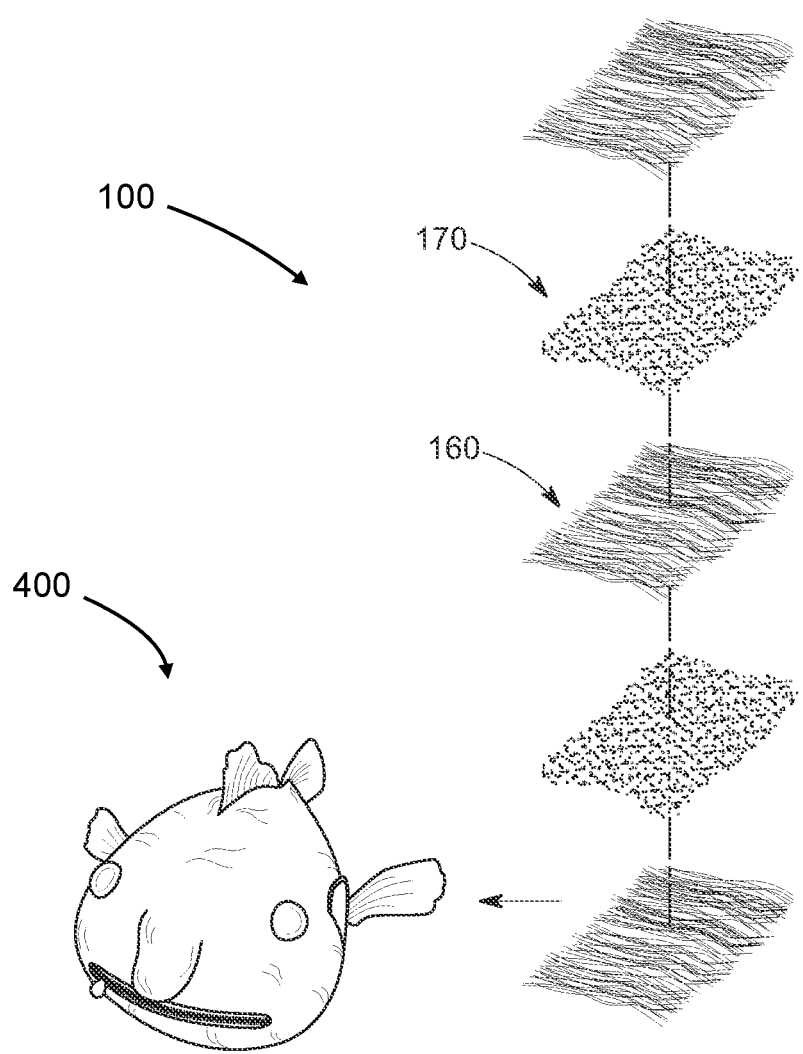
FIG. 8 is an illustration showing the salt holding pillow integrated into a second stuffed animal.

In one or more non-limiting embodiments, salt holding pillow system 100 may be incorporated into a plush, or stuffed toy 400 that is configured to appear like an otherwise traditional teddy bear as illustrated in FIG. 4 and FIG. 8. The teddy bear and fish are merely illustrative and instead stuffed toy 400 may be any other living creature, e.g. animals such as a monkey, rabbit, dog, fox, cat, lion etc., or as a human doll figure as well as be a different type of toy such as a pet toy 500 (cat nip) as illustrated in FIG. 5. Salt holding pillow system 100 may be positioned inside of stuffed toy 400 whereby the opening may be covered with strips of hook and loop fastener, such as Velcro®, a zipper, or other fastening mechanism. In further embodiments pillow system 100 may be built into stuffed toy 400 during manufacturing process. In some embodiments salt holding pillow system 100 may be incorporated into a second apparatus complimentary to stuffed toy 400 such as something the stuffed toy 400 is holding.

Figure 6:
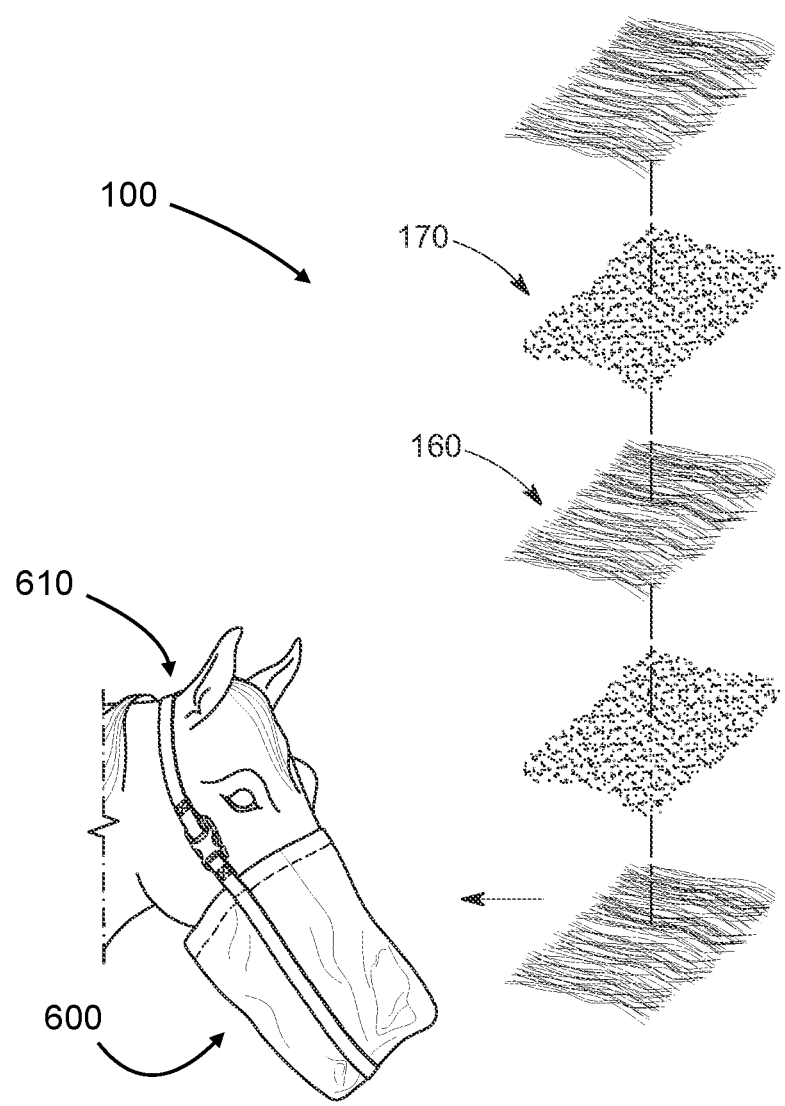
FIG. 6 is an illustration showing the salt holding pillow integrated into a feed bag.

In one or more non-limiting embodiments, salt holding pillow system 100 may be incorporated into an animal inhalation mask 600 or feed bag, such as whereby an inhalation mask 600 is fitted over a horse's snout as illustrated in FIG. 6. In this embodiment, inhalation mask 600 is held in position on the horse's snout by adjustable head strap 610. Head strap 610 is configured to wrap around the horse's head and sits behind its ears to hold inhalation mask 600 position. Head strap 610 is attached to inhalation mask 600 by any number of fasteners such as but not limited to latches, straps hinges, or buckles. Salt holding pillow system 100 may be preferably located towards the bottom of the mask proximate to the horse's mouth to facilitate a more relaxed breathing environment.

Figure 7:
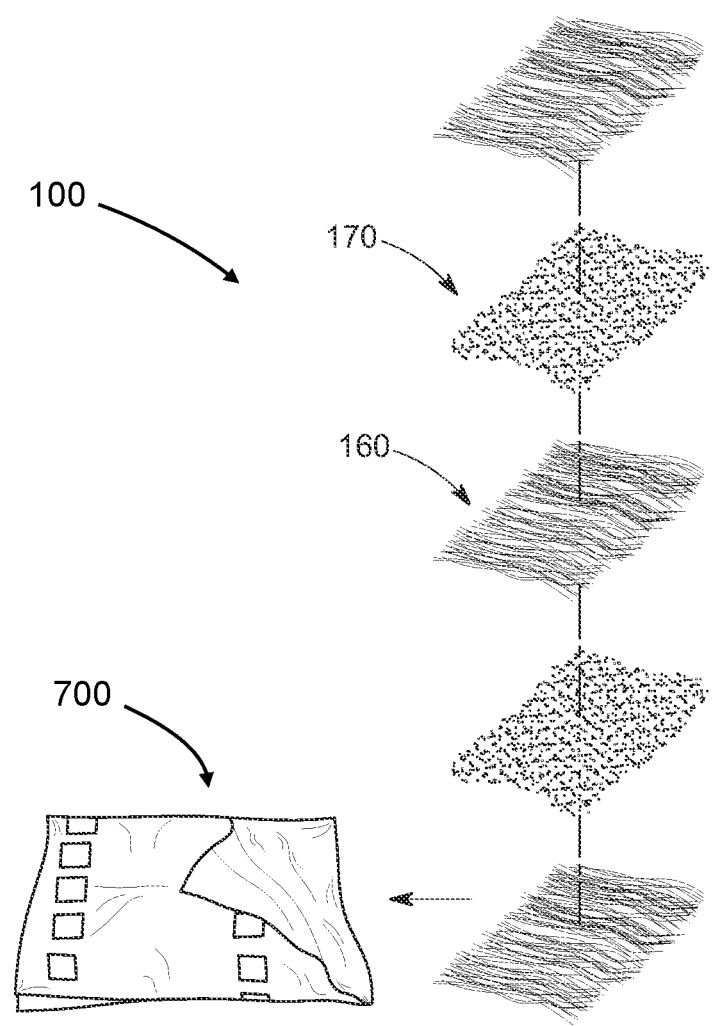
FIG. 7 is an illustration showing the salt holding pillow integrated into a scrubbing sleepingbag-type roll.

In one or more non-limiting embodiments, salt holding pillow system 100 may be incorporated into scrubbing sleeping bag-type roll 700 as illustrated in FIG. 7. Bed roll 700 comprises an outer lining and a lower lining having a pair of inner linings comparing salt holding pillow system 100 there in between which form a four-layered structure defining an elongated, rectangular configuration. While the present invention is described as having four linings, it should be understood and anticipated that any number of linings may be utilized. Similarly pillow system 100 may be integrated into a pillow or pillow case.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A salt holding system comprising: a salt holding apparatus having one or more wool layers of fiber, the one or more wool layers infused with salt; and a face mask, wherein the salt holding apparatus is removably inserted into a pocket of the face mask, the pocket positioned inside of a nose cover of the face mask.

2. A salt holding system comprising: a salt holding apparatus having one or more wool layers of fiber, the one or more wool layers infused with salt; and a stuffed toy, wherein the salt holding apparatus is positioned into an interior of the stuffed toy.

3. A salt holding system comprising: a salt holding apparatus having one or more wool layers of fiber, the one or more wool layers infused with salt; and a feeding mask, wherein the salt holding apparatus is integrated into an interior of the feeding mask, the feeding mask connected to a head strap, the head strap configured to be positioned around a head of an animal.

4. A salt holding system comprising: a salt holding apparatus having one or more wool layers of fiber, the one or more wool layers infused with salt; and a bed roll, wherein the salt holding apparatus is integrated into one or more intermediate layers of the bed roll, the bed roll having an exterior and interior layer, the one or more intermediate layers positioned between the exterior and interior layer to form a structure defining an elongated, rectangular configuration.

5. A salt holding pillow, the salt holding pillow having a first section having a first wool layer, salt placed on the first wool layer, and a second wool layer positioned above the first wool layer.

6. The salt holding pillow of claim 5, further comprising a second amount of salt placed on the second wool layer and a third wool layer positioned above the second amount of salt.

7. The salt holding pillow of claim 5, the first wool layer and the second wool layer made of wool fibers that have been pulled apart and formed to create a rectangular shape.

8. The salt holding pillow of claim 5, wherein the salt is pharmaceutical grade salt, pink Himalayan salt, or sea salt that is ground into a powder.

9. The salt holding pillow of claim 5, further comprising rice or silica used as a desiccant.

10. A salt holding pillow, the salt holding pillow having multiple layers of fiber and salt positioned between two or more of the multiple layers.

11. The salt holding pillow of claim 10, wherein the multiple layers are made of wool.

* * * * *